United States Patent [19]
Krumme

[11] Patent Number: 4,713,063
[45] Date of Patent: Dec. 15, 1987

[54] INTRAVENOUS TUBE AND CONTROLLER THEREFOR

[75] Inventor: John F. Krumme, Woodside, Calif.

[73] Assignee: Beta Phase, Inc., Menlo Park, Calif.

[21] Appl. No.: 857,974

[22] Filed: May 1, 1986

Related U.S. Application Data

[63] Continuation-in-part of Ser. No. 733,036, Apr. 29, 1985, Pat. No. 4,645,489, which is a continuation of Ser. No. 445,390, Nov. 30, 1982, abandoned.

[51] Int. Cl.$^4$ ............................................. A61M 5/00
[52] U.S. Cl. ..................................... 604/250; 604/34; 251/6
[58] Field of Search .................. 604/34, 153, 250; 417/474–477; 251/4–10

[56] References Cited

U.S. PATENT DOCUMENTS

| | | | |
|---|---|---|---|
| 2,123,781 | 7/1938 | Huber | 417/476 |
| 3,128,716 | 4/1964 | Stallman et al. | 417/474 |
| 3,192,863 | 7/1965 | Vadot | 417/477 |
| 3,403,238 | 9/1968 | Buehler et al. | 251/11 X |
| 3,403,631 | 10/1968 | Tangeman | 417/475 |
| 3,613,732 | 10/1971 | Willson et al. | 251/11 X |
| 3,778,195 | 12/1973 | Bamberg | 417/474 |
| 3,985,134 | 10/1976 | Lissot et al. | 604/34 X |
| 3,990,443 | 10/1975 | Fletcher | 604/65 |
| 3,991,972 | 11/1976 | Eaton | 251/11 |
| 4,087,301 | 5/1978 | Steadman | 251/6 X |
| 4,105,028 | 8/1978 | Sadlier et al. | 604/65 |
| 4,137,940 | 2/1979 | Faisandier | 137/486 |
| 4,261,388 | 4/1981 | Shelton | 604/65 X |
| 4,265,240 | 5/1981 | Jenkins | 128/214 |
| 4,300,552 | 11/1981 | Cannon | 128/214 |

FOREIGN PATENT DOCUMENTS

| | | | |
|---|---|---|---|
| 0062365 | 10/1982 | European Pat. Off. | |
| 2733702 | 2/1979 | Fed. Rep. of Germany | |
| 2479914 | 10/1981 | France | 604/153 |
| WO82/01651 | 5/1982 | PCT Int'l Appl. | |
| 1578741 | 11/1980 | United Kingdom | 251/11 |
| 2054200 | 2/1981 | United Kingdom | |

OTHER PUBLICATIONS

Journal of Metals, vol. 32, No. 6, Jun. 1980, pp. 129–137, New York, C. M. Wayman: "Some Applications of Shape-Memory Alloys."

Primary Examiner—Dalton L. Truluck
Attorney, Agent, or Firm—Burns, Doane, Swecker & Mathis

[57] ABSTRACT

A tube for use in a flow controller of an intravenous or other slow flow control apparatus has a configuration somewhat like the opening defined by the open eyelids of the human eye whereby to provide relatively sharp corners and narrow width of the opening to reduce materially the force required to close relative to that required to close a round tube and to reduce the movement of the flow control element of the controller, which controller is configured to take advantage of the shape of the tube and employs a shape memory control element to adjust rate of flow of the fluid; the controller also including a brake element to lock the flow rate at a particular preselectable rate.

4 Claims, 9 Drawing Figures

T = Temperature
I = Electric Current

INTRAVENOUS TUBE AND CONTROLLER THEREFOR

RELATED MATERIALS

This application is a continuation-in-part to patent application Ser. No. 733,036 filed Apr. 29, 1985, now U.S. Pat. No. 4,645,489, in the names of John F. Krumme and Darel Hodgson, which is in turn a continuation of Ser. No. 445,390 filed Nov. 30, 1982, now abandoned, the disclosures of which are incorporated herein by reference.

The present invention forms the subject matter of Disclosure Document #141799 filed Oct. 2, 1985 by John F. Krumme, the disclosure of which is also incorporated herein by reference.

BACKGROUND OF THE INVENTION

The present invention relates to tubing for use in and an intravenous flow controller and more specifically to a novel internal cross-sectional shape of such tubing and a novel flow controller for taking advantage of the novel internal cross-sectional shape of the tubing as well as additional novel features.

Controllers for controlling the drop or flow rate through an intravenous tube are well known in the art and are exemplified by devices illustrated in U.S. Pat. Nos. 3,991,972, 4,137,940 and 4,300,552. The forces required of such devices to completely block flow through the standard round I.V. tube are typically as much as three pounds. Only a relatively small amount of the force is required to close the main body of the tube, the majority of the force being required to close small circular openings at the outer edges of the compressed tube, a phenomenon commonly known as the dog-bone effect. The high pressure required to close round tubing will deform the tube wall. Upon release of the pressure, during initial fluid flow, the deformation in the tube wall requires time to return to its original thickness. This element of time undesirably affects the response time of the control device. In addition, due to the high forces required to fully close the round tubing, when pressure is released the tubing will have a tendency to stick together.

BRIEF DESCRIPTION OF THE PRESENT INVENTION

In accordance with the present invention a flow control tube in the form of an intravenous tube of a novel configuration is employed to reduce by as much as 90% the force required to close the tube. The invention also contemplates a novel control mechanism designed to take advantage of the improvements provided by the novel tube configuration.

The tube may be formed from an initially round plastic tube of suitable inherently resilient material such as polyvinylchloride which has a diameter and wall thickness that is standard for the industry; approximately 0.143 inch O.D., and 0.105 inch I.D., thus providing a wall thickness of approximately 0.019 inch. According to the method employed to form the tube of the present invention, a mandrel is inserted in such tubing and this length of tube surrounding the mandrel is heated in a mold to produce an internal cross-section defined by symmetrical catenary shaped wall portions terminating in opposed sharp internal corners which looks like the opening of the eye when the lids are open or even like an oyster shell with a slightly larger height than average. Thus, the interior of the wall portions of the tube come together in sharp corners and curve outwardly to meet in a gentle curve in the middle of the wall portions. When the opposing wall portions of the opening are moved toward one another the opening flattens out with no dog-bone effect and the forces required to close the tube are greatly reduced.

It is within the scope of the invention to form the finished tube of the present invention by methods other than reforming a round tube. Specifically, the novel flow control tube may be formed by precision extrusion, lamination or blow molding techniques as well as other methods of forming a tubing having a dimensionally precise cross-section.

The wall thickness of the finished tube of the example is important since it must be thick enough to have sufficient resilient force to open in spite of the hydrostatic forces tending to hold the opposing interior surfaces of the plastic together after the tube has been completely collapsed. If the walls are too thin they tend to adhere to one another and are slow to open, requiring hydrostatic pressure build-up to reopen the tube.

On the other hand, the walls of the reconfigured tube should not be so thick that large forces are required to move the walls of the tube, thus increasing response time and requiring a controller capable of delivering much greater forces and rapid response. In the present invention, a final wall thickness of the reconfigured tube is about 0.015 inch with an interior length of opening of about 0.142 inch with an interior height of about 0.06 inch. Such a tube requires a force of about ½ pound to stop flow whereas a round tube of the same material requires about 3 pounds to fully close.

The specific size and precise shape of a reconfigured tube is a function of the initial tube diameter, wall thickness, tube material and the liquid to be controlled. The example given above and described in greater detail hereinafter is intended to be considered only as exemplary of a specific tube.

The tube is reconfigured by inserting a mandrel of the desired final shape and size into the tube, compressing the exterior of the tube in a mold and heating the mold and tube to produce a permanently reconfigured shape.

The controller of the present invention utilizes a relatively sharp edge on one end of a right-angle lever to compress the reconfigured tube. The lever is actuated by a shape-memory alloy element, preferably in the form of Nitinol wire, and a brake mechanism is provided which can lock the lever in a desired fixed position. The brake may also be Nitinol-controlled.

The controller is configured such that the sharp edge of the lever engages the tube at right angles to an opposing tube-abutting surface when the tube is fully closed, such operation being possible due to the relatively small width of the reconfigured tube. Such operation insures complete closing with the least amount of force for a given system.

Accordingly, a first aspect of the present invention provides a flow control tube comprising a hollow elongated tube through which fluid may flow, said tube having a generally continuous side wall wherein at least a portion of said tube has an internal cross-section defined by symmetrical catenary shaped wall portions joining in opposed sharp internal corners, said wall portions capable of being moved toward each other to flatten said tube and control fluid that may flow therethrough.

A second aspect of the present invention provides an intravenous flow rate controller comprising a pivoted lever having a knife edge projecting therefrom; a passage for receiving a tube through which intravenous fluid is to flow; a wall projecting into said passage opposite said knife edge; and a pivot for said lever disposed relative to said wall such that said knife edge approaches and retreats from said wall upon pivoting of said lever and lies generally in a plane perpendicular to said wall upon engagement therewith.

A third aspect of the present invention provides a method of changing the configuration of a flexible plastic tube comprising the steps of:

inserting a mandrel of the desired internal cross-sectional shape into the tube;

clamping at least a portion of the region of said tube into which the mandrel has been inserted in a clamp having opposed surfaces which define an interior cavity having approximately the same shape as the cross-section of the mandrel;

heating the mold to a temperature and for a time to cause reflow of the material of the tube; and removing the tube from the mold and the mandrel from the tube.

DETAILED DESCRIPTION OF THE INVENTION

Figure 5:
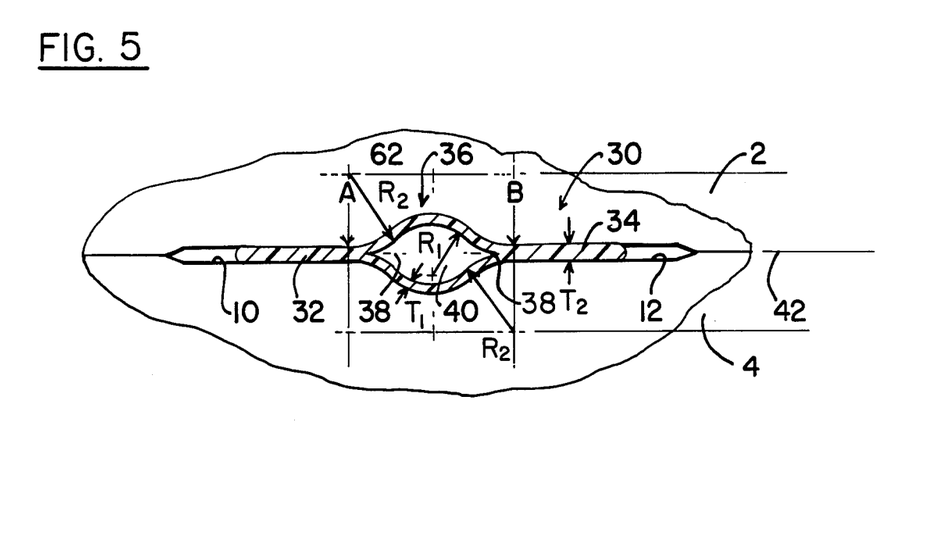
FIG. 5 is a view in cross-section of the tube of the present invention positioned within the mold of FIG. 1.

Referring specifically to FIGS. 1, 2, 3 and 4 there is illustrated the mold (FIG. 1) and mandrel (FIG. 2) required to produce the flow control tube of FIG. 5.

Figure 1:
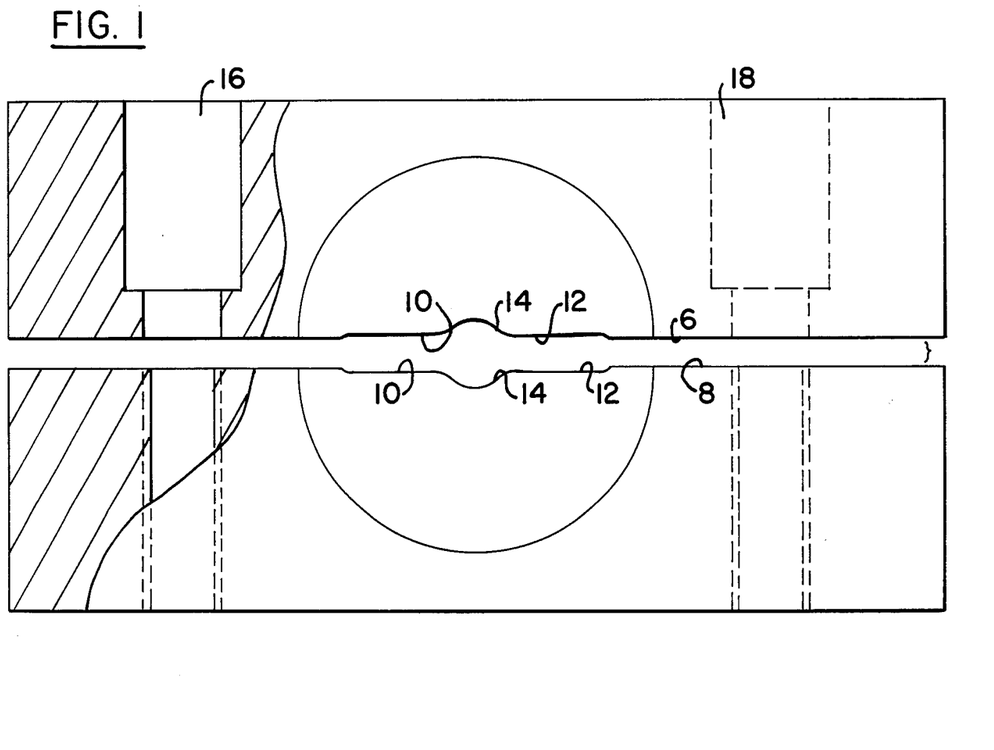
FIG. 1 is a side view in elevation of a mold employed to form the tube of the present invention.

The mold comprises a pair of aluminum blocks 2 and 4 which have opposed surfaces 6 and 8 machined to provide matching relieved surfaces. Each surface has regions 10 and 12 on either side of center of a machined-out depth of about 0.012 inch, thus providing a space therebetween of 0.024 inch when the blocks are clamped together unless shims are employed as hereinafter explained. Centrally located between the ends of regions 10 and 12 of each block is a generally arcuate region 14 of increased height. The length of each region 14 is about 0.175 inch and the depth perpendicular to the page is approximately 0.44 inch. The blocks may be clamped together by two bolts 16 and 18, having their heads seated in block 2 and threaded into block 4.

Figure 2:
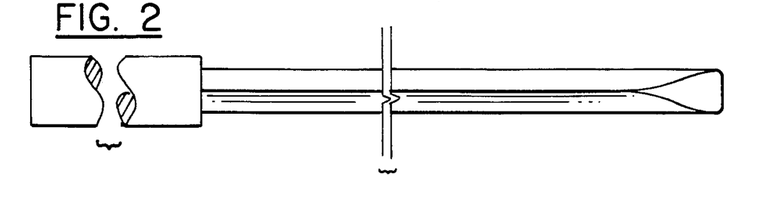
FIG. 2 is a side view in elevation of the mandrel employed to mold the tube of the invention.
Figure 3:
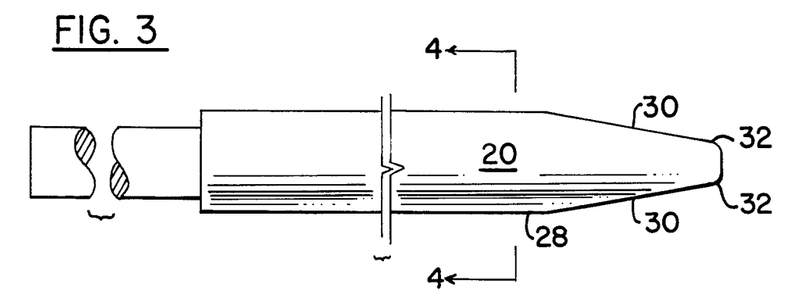
FIG. 3 is a top view of the mandrel.
Figure 4:
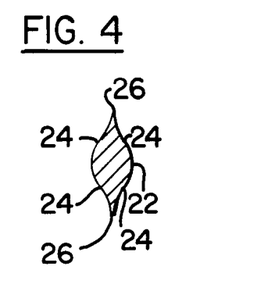
FIG. 4 is a view in cross-section of the mandrel taken along line 4—4 of FIG. 3.

Tooling also includes a mandrel 20, as illlustrated in FIGS. 2 and 3, which is to be inserted into the tube prior to clamping in the mold. The mandrel in this example has a width of approximately 0.142 inch, a maximum thickness of 0.06 inch, a radius at its end region 24 of 0.083 inch and intersecting at points 26 at the two ends.

Body 28 of the mandrel 20 is tapered along both edges 30 and rounded at its corners 32 to permit ease of insertion into the tube.

In operation the mandrel 20 is inserted into one end of a length of plastic tubing and the tubing is clamped between the blocks 2 and 4. The blocks are then heated to about 200° C. for a short time such as about 2 to 3 minutes to reflow the polyvinylchloride, producing the shape of tube 30 illustrated in FIG. 5 of the accompanying drawings. It can be seen that the generally continuous sidewall of the hollow elongated tube has an internal cross-section defined by symmetrical caternary shaped wall portions terminating in opposed sharp internal corners 38. The mandrel 20 has an external cross-section complementary to the finished tube shape. The regions of the tube that are clamped between regions 10 and 12 of the blocks are fused together to produce end regions 32 and 34. The tubing disposed about the mandrel 20 is configured in a caternary shape as at 36 with a center region having an internal radius $R_1$ for each wall portion of about 0.062 inch and the end regions having a reverse radii $R_2$ of about 0.07 inch, such that the wall portions join approximately tangentially in opposed sharp corners. The internal radius $R_1$ and the reverse radii $R_2$ are approximately equal.

The relationship between the internal radius and the reverse radii must be chosen to provide:

(1) sufficiently sharp internal radius to provide adequate opening force;

(2) an approximate joining of the opposed wall portions;

(3) a smooth transition between the center region and the end regions; and (4) an internal cross-section that is adequate for the desired flow rate.

This can be achieved when the internal radius and the reverse radii are close to equal.

In order for a controller to close the opening in the tube, a knife edge 62 is applied parallel to center line 42 along one of the surfaces of the tube over the region between points A and B of FIG. 5, the opposed surface of the tube abutting a wall so that the tube is easily closed with low force and small movement of the knife edge to move the wall portions toward each other to flatten the tube and control flow therethrough.

Figure 6:
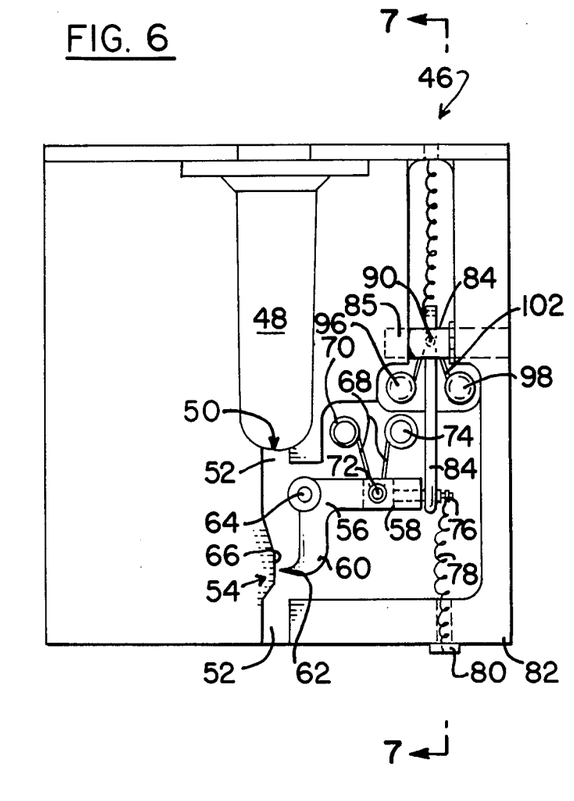
FIG. 6 is a front view in elevation of the controller of the present invention.
Figure 7:
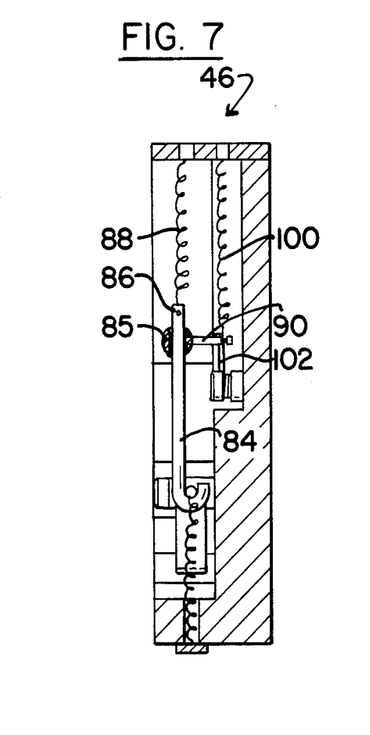
FIG. 7 is a section view of the controller of FIG. 6 taken along lines 6—6 of FIG. 6.

Reference is now made to FIGS. 6 and 7 of the accompanying drawings which illustrate the controller of the present invention. The controller, generally designated by the reference numeral 46, has a drop chamber cavity 48 with an opening 50 at the bottom to feed one end of the tube of FIG. 5 which is secured in a channel 52 of circular cross-section. A drop chamber assembly may be placed in cavity 48 and attached to the top end of the tube 30. The reformed region 36 of tube 30 is situated at inward projection 54 of the left wall, as viewed in FIG. 6, of the passage 52. The pivotal lever 56 has a horizontal arm 58 and a vertical arm 60 terminating in a horizontal knife edge 62 directed toward the projection 54, all as viewed in FIG. 6. The lever 56 is pivoted about a horizontal pivot pin 64 disposed relative to the wall 66 so that the knife edge 62 may be moved toward and away from the opposing wall 66 of the projection 54, the wall 66 projecting into the passage opposite the knife edge 62. The projection 54 is required to permit the pivot pin 64 of the lever 56 to be located so that the knife edge 62 lies in a plane perpendicular to the wall 66 when in engagement with the wall to thereby insure maximum closing force at the time of full closure of the passage.

The tube 30 is located in channel 52 such that the region 36 of the tube lies between the wall 66 and the knife edge whereby movement of the lever 56 causes the knife edge 62 to close the tube to varying degrees depending upon the desired drop rate.

Control of the lever 56 is accomplished by a wire 68, hereinafter the "first shape-memory member", of shape-memory material, preferably Nitinol, which extends from a first electrical terminal 70 downward into operative contact with the lever 56 under a horizontal pin 72 extending outwardly from the arm 58 of the lever 56, and upwardly to a second electrical terminal 74. It is, of course, within the scope of the invention to have the first shape-memory member be of alternate configuration such as a cantilevered lever, etc. (not shown) and in operative contact with lever 56. Sticking out of the end of the arm 58 remote from the pin 64 is another horizontal pin 76. The pin 76 is engaged by a tension spring 78, hereinafter the "first spring", extending downwardly from the pin 76 to a spring-engaging plate 80 secured to frame 82 of the controller 46.

First spring 78 pulls down on the pin 76 to rotate the lever 56 clockwise to cause the knife edge 62 to approach wall 66 and close the tube 30, i.e. to bias the knife edge 62 into engagement with said wall. The Nitinol wire, when energized by passing electrical current through the wire, thus raising the wire's temperature by resistance heating, opposes and counters the force of the first spring 78 to varying degrees to control flow rate.

It is well known that, in the temperature range where Nitinol transforms between the austenitic and martensitic states, the alloy exhibits a continuous variation in its mechanical properties with temperature. In the case of a Nitinol wire with initial length $L_o$, the mechanical behavior can be represented by the force F required to elongate the wire by a change in length L. The force-versus-length curves for Nitinol at selected temperatures in the transformation temperature range (TTR) ar shown in FIG. 9.

Figure 9:
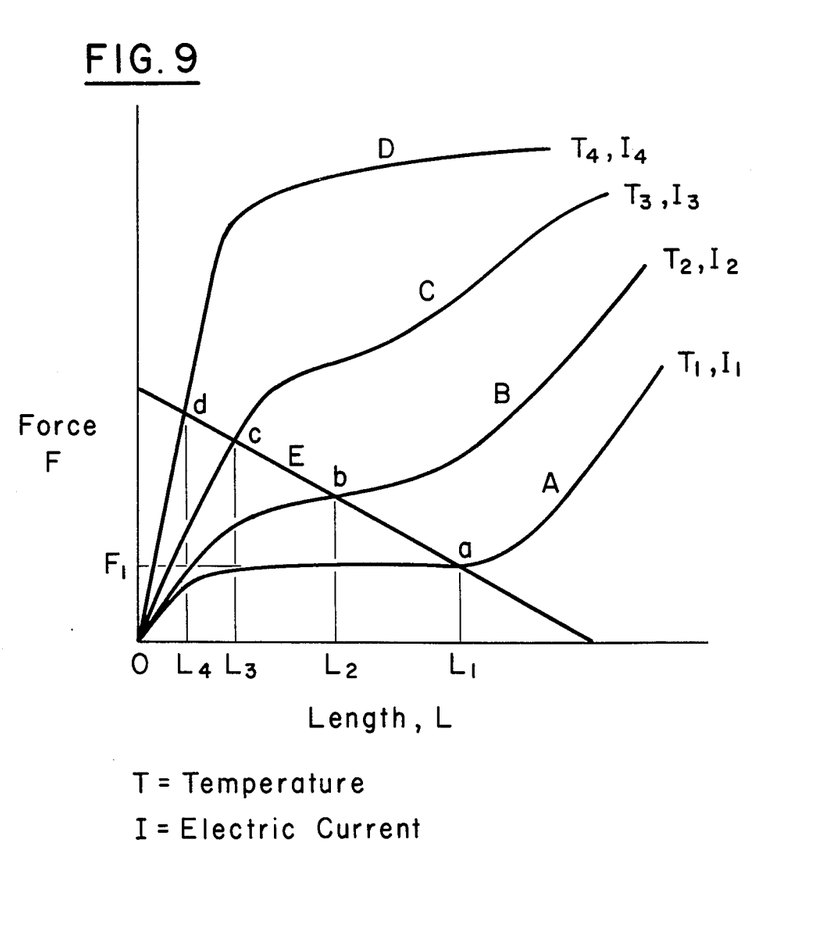
FIG. 9 is a graph of force-vs-length curves for Nitinol at selected temperatures in the transformation temperature range.

At temperature $T_1$, the alloy is fully martensitic and can be stretched a relatively large amount, $L_1$, corresponding to about 8% strain, at a relatively low and constant force $F_1$. When the Nitinol wire is heated without applied stress to the austenitic state at $T_4$, the length returns to $L_o$ by the shape-memory effect. At temperatures between $T_1$ and $T_4$ the curves change from Curve A to Curve D type behavior and the amount of heat-recoverable strain decreases. At $T_4$ there is no heat-recoverable strain. Intermediate Curves B and C corresponding to intermediate temperatures $T_2$ and $T_3$ are shown in FIG. 9 as examples.

Consider a Nitinol wire which is elongated by the applied force from a conventional elastic spring so that the Nitinol wire stretches as the spring compresses and vice versa. The stress-strain curve of the spring is defined by the straight line, E.

The Nitinol, at temperature $T_1$, can be stretched by the spring out to length $L_1$. If the Nitinol is then heated it will attempt to recover its strain by the shape-memory effect but must work against the spring to do so. As the temperature increases, the Nitinol follows the path abcd defined by the intercepts of the spring's force-length curve, E, which is essentially independent of temperature, and the family of temperature-dependent Nitinol force-length curves, A, B, C, D.

If the Nitinol temperature is controlled by resistively heating the length of Nitinol wire, each temperature $T_1$, $T_2$, $T_3$, $T_4$ corresponds to a current $I_1$, $I_2$, $I_3$, $I_4$. Thus by varying the current and hence the temperature, the Nitinol wire can be precisely controlled to a corresponding length $L_1$, $L_2$, $L_3$, $L_4$.

Although only Nitinol has been discussed herein, various changes in properties are affected by additives, heat treatment and work hardening. Further, Cu-Zn-Al and other copper-based and like alloys are also specifically useful herein, having many of the same types of characteristics as Nitinol. See, for instance, "Shape Memory Alloys", Page 728, Vol 20, of *Kirk-Othmi's Encyclopedia of Chemical Technology*, John Wiley & Sons, Third Edition.

A further feature may be added to the present invention. As described above, heating power (electrical current) must be continuously applied to maintain a given knife edge 62 position and thus a given fluid flow rate. A further feature of the present invention is a brake means whereby the desired knife edge position can be maintained with power removed from the first shape-memory member. This brake means may be implemented using a second shape-memory member as the actuator force so that the brake means is free when power is applied to the second shape-memory member and locked when power is removed. This provides an actuator that can be precisely adjusted by sequentially removing power from the second and then the first shape-memory members and will maintain this precise adjustment with no power applied to either of the shape-memory members.

An embodiment of the brake means in the form of a J-shaped brake rod 84 has its bottom loop disposed under the pin 76 and its riser extends upward through a passage through a cylindrical bushing 85. The upper end of the rod 84 has a hole 86 to receive one end of a tension spring, hereinafter "second spring", that pulls up on the rod with a much smaller force than first spring 78 pulls down on the pin 76 and thus the brake rod. The bushing 85 is rotatable about its cylindrical axis and has a horizontal pin 90 extending into the cylindrical wall of bushing 85 in a generally horizontal plane.

Figure 8:
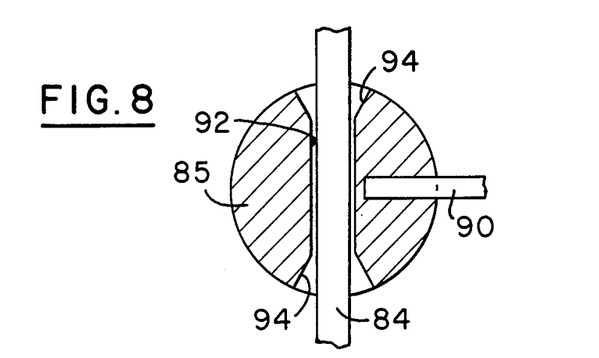
FIG. 8 is a detailed enlarged cross-sectional view of a part of the bushing and brake rod of FIG. 6.

The bushing 85, rod 84 and pin 90 are illustrated in greater detail in FIG. 8. The bushing 85 has a cylindrical aperture 92 that slidably, but snuggly, receives the rod 84. The two ends of the aperture are tapered outwardly at 94 so as to permit the bushing to be rotated in either direction. When so rotated the opposed edges of the tapers 94 of the aperture 92 engage the rod and in effect wedge it in place.

The pin 90 is engaged by a second shape-memory member in the form of a shape-memory metal wire 102, which again may be Nitinol. The wire 102 extends from contacts 96 and 98 located below the pin 90 and over it. When the wire is cool, it may be stretched by a third spring 100 extending vertically from the pin 90 upwardly to a frame member biasing the pin away from the third spring 100. When the wire is cool, the third spring 100 pulls up on the pin and locks the rod 84 in place by rotating the cylindrical bushing 85. When the wire is heated by an electrical current, the second shape memory member in the form of the Nitinol wire pulls down on the pin 90; the rod 84 is then free to move and is pulled up against pin 76 and thus the brake rod will faithfully follow movement of lever 56.

In operation, the rod 84 is held in position by rotation of bushing 85, and the knife edge 62 is in contact with tubing segment 30 which is between the knife edge and the wall 66. The wire 102 is heated by passing a current therethrough and the rod is released but does not move since the spring 78 is stronger than the spring 88 and the force of the wire 68 in its elastic state. Thereafter current is applied to the wire 68 and is adjusted so that the upward force produced by wire 68 moves the knife edge to a position where the drop rate in the chamber 48 is as desired.

It should be noted that the second spring 88 maintains the rod 84 in contact with pin 90 so that if the wire 102 is deenergized and then a short time later the wire 68 is deenergized the lever is locked in its last position; the rod 84 prevents the pin 76 from moving down and the spring 78 prevents it from moving up. Thus, the controller may be "parked" at a particular nominal drop rate. Such operation may be beneficial because power doesn't have to be maintained except when readjusting the restriction and a nominal drop rate is preferable to the danger of a radically wrong rate in a situation where the current control mechanism malfunctions.

It is within the scope of the invention to employ alternate brake means (not shown) such as an electrically actuated caliper brake, a clutch plate device, or other mechanical expedients that would be capable of selectively locking the lever 56 when in a preselected rotated position with respect to the lever's pivot when power is removed.

Various changes and alternatives to the above tube and controller are readily apparent. As previously mentioned, the specific details of the tube (size, wall thickness, materials, etc.) will vary with the specific fluids with which the controller is to be employed and the flow rate of the fluid. Also such a tube configuration has utility in other flow rate control devices, particularly in chemical systems.

The controller is of general utility being of use wherever a flow rate or actuator position needs to be set or maintained at a given position for some period of time and relatively low rates of flow are to be controlled. Further, although tension springs are employed, compression springs or safety-pin-like springs are also useful.

The molding function is useful in small quantities but other forming techniques may be employed.

Other improvements, modifications and embodiments will become apparent to one of ordinary skill in the art (upon review of this disclosure). Such improvements, modifications, and embodiments are considered to be within the scope of this invention as defined by the following claims.

I claim:

1. An I.V. flow control tube adapted to be used in an I.V. control wherein the metering characteristics of the tube require the repeated controlled closing and time responsive opening of the tube in operation, the tube consisting essentially of a hollow elongated tube of resilient material through which fluid may flow, said tube having a reformed section which has an internal cross-section defined by symmetrical catenary shaped wall portions joining approximately tangentially in opposed sharp internal corners, said section of said tube having a center region having an internal radius for each catenary shaped wall portion, said section of said tube having end regions each having an external reverse radius for each wall portion such that the wall portions join approximately tangentially in opposed sharp internal corners and wherein the internal radii and said external reverse radii are approximately equal within the range of about 0.75 to 1.25, said wall portions capable of being moved toward each other to flatten said tube and control fluid that may flow therethrough, the shape of said cross-section in combination with resilient recovery forces inherent in said material producing a residual reopening force.

2. An intravenous flow rate controller assembly comprising:
   a knife edge;
   a passage for receiving a tube through which intravenous fluid may flow;
   a wall projecting into said passage opposite said knife edge, said knife edge moveable toward and away from said wall; and
   a tube of resilient material positioned within said passage, said tube being generally vertically oriented and having an inlet section connectable to an intravenous fluid supply and a relatively long outlet section as compared to said inlet section connectable to a patient, said inlet and outlet sections separated by a reformed section, said reformed section positioned between said wall and said knife edge, said reformed section of said tube having an internal cross-section defined by symmetrical catenary shaped wall portions joining approximately tangentially and in opposed sharp internal corners, said section of said tube having a center region having an internal radius for each catenary shaped wall portion, said section of said tube having end regions each having an external reverse radius for each wall portion such that the wall portions join approximately tangentially in opposed internal sharp corners and wherein the internal radii and said external reverse radii are approximately equal within the range of about 0.75 to 1.25, said wall portions capable of being moved toward each other by said knife edge to flatten said tube and to control fluid that may flow therethrough, the flattening of said tube causing negative hydrostatic pressure in said outlet section, said negative hydrostatic pressure tending to hold said reformed section closed, the shape of said cross-section in combination with resilient recovery forces inherent in said material producing a residual reopening force.

3. An assembly as in claim 2 further comprising:
   a first spring in operative contact with said knife edge for biasing said knife edge into engagement with said wall; and
   a first shape-memory member in operative contact with said knife edge, said first shape-memory member when heated capable of countering the force of said spring and causing said knife edge to move away from said wall to an extent determined by the degree of heating of said first shape-memory member.

4. An assembly as in claim 3 wherein said first shape-memory member is a wire that is shortened upon heating.

* * * * *

UNITED STATES PATENT AND TRADEMARK OFFICE
CERTIFICATE OF CORRECTION

PATENT NO. : 4,716,063  Page 1 of 3
DATED : December 29, 1987
INVENTOR(S) : HARUO UEHARA, ET AL.

It is certified that error appears in the above-identified patent and that said Letters Patent is hereby corrected as shown below:

COLUMN 2

Line 29, "mothacryic" should read --methacrylic--.
    Line 39, "layer." should read --layer,--.
    Line 57, "liqid" should read --liquid--.
    Lines 61-62, tranferred" should read --transferred--.
    Line 67, "marcapto" should read --mercapto--.

COLUMN 3

Line 3, "cross sectional" should read --cross-sectional--.
    Line 5, "cross sectional" should read --cross-sectional--.
    Line 5, "twoside" should read --two-side--.
    Line 7, "adhored" should read --adhered--.
    Line 8, "cross sectional" should read --cross-sectional--.
    Line 10, "cross sectional" should read --cross-sectional--.
    Line 12, "cross sectional" should read --cross-sectional--.
    Line 13, "adherod" should read --adhered--.
    Line 23, "formula;" should read --formula:--.

COLUMN 4

Line 37, "." should read --,--.
    Lines 38-39, "ß-mercaptethyltriethoxysilane." should read
          --ß-mercaptoethyltriethoxysilane.--.

UNITED STATES PATENT AND TRADEMARK OFFICE
CERTIFICATE OF CORRECTION

PATENT NO. : 4,716,063
DATED : December 29, 1987
INVENTOR(S) : HARUO UEHARA, ET AL.

It is certified that error appears in the above-identified patent and that said Letters Patent is hereby corrected as shown below:

COLUMN 5

Line 18, "30 agent" should read --30 mm at the central portion thereof. The silane coupling agent--.
Line 19, "γ-methacryloxypropy trimethoxysilane" should read --γ-methacryloxypropyltrimethoxysilane--.
Line 24, "10 mm thick" should read --10 mm-thick--.
Line 40, "of isopropyl" should read --of benzoin isopropyl--.
Table 1, "Pentaerthritolte-"
    traacrylate        should read
    --Pentaerythritolte---
    traacrylate
Table 1, "Peelability From
    Stamper △ △ △ "
    should read
    --Peelability From
    Stamper ○○○○○○△○○○○△○○○△○○--
Table 1, "Durability of"
    Magnetic Film
    should read
    --Durability of
    Magnetic Film ○○○○○○○○○○○○○○○○○○○--

COLUMN 6

Line 5, "was at" should read --was slightly inserted between the stamper and the resin at--.
Line 15, "cross-out" should read --cross-cut--.

UNITED STATES PATENT AND TRADEMARK OFFICE
CERTIFICATE OF CORRECTION

PATENT NO. : 4,716,063
DATED : December 29, 1987
INVENTOR(S) : HARUO UEHARA, ET AL.

It is certified that error appears in the above-identified patent and that said Letters Patent is hereby corrected as shown below:

COLUMN 6 (continued)

Lines 31-32, "methacryloxpropane;" should read
        --methacryloxypropane;--.
    Line 34, "dimethacylate;" should read --dimethacrylate;--.

COLUMN 7

Table 2, "Pentaerthritoltetraacrylate" should read
        --Pentaerythritoltetraacrylate--.
    Table 2, "Peelability From Stamper     X    X " should read
        --Peelability From Stamper OO X OOOOO X --

COLUMN 8

Line 9, "off." should read --off,--.
    Line 20, "a" should read --as--.

Signed and Sealed this

Tenth Day of May, 1988

Attest:

DONALD J. QUIGG

Attesting Officer         Commissioner of Patents and Trademarks

UNITED STATES PATENT AND TRADEMARK OFFICE
CERTIFICATE OF CORRECTION

PATENT NO. : 4,713,063

DATED : December 15, 1987

INVENTOR(S) : John F. Krumme

It is certified that error appears in the above-identified patent and that said Letters Patent is hereby corrected as shown below:

Column 2, line 64, "caternary" should be --catenary--.

Column 4, line 14, "caternary" should be --catenary--.

Column 4, line 21, "caternary" should be --catenary--.

Column 5, line 41, "ar" should be --are--.

Column 8, lines 28 and 29, "caternary" should be --catenary--.

Signed and Sealed this

Sixteenth Day of August, 1988

Attest:

DONALD J. QUIGG

*Attesting Officer*     *Commissioner of Patents and Trademarks*